United States Patent [19]

Aruny

[11] Patent Number: 5,207,649
[45] Date of Patent: May 4, 1993

[54] INTRODUCER SHEATH HAVING A HEMOSTATIC CLOSURE

[75] Inventor: John E. Aruny, Arlington, Mass.

[73] Assignee: Brigham and Women's Hospital, Boston, Mass.

[21] Appl. No.: 806,308

[22] Filed: Dec. 13, 1991

[51] Int. Cl.$^5$ .............................................. A61M 5/00
[52] U.S. Cl. .................................. 604/167; 251/149.1
[58] Field of Search ................ 604/164, 158, 159, 161, 604/167, 169, 256; 137/846; 251/149.1

[56] References Cited

U.S. PATENT DOCUMENTS

| | | | |
|---|---|---|---|
| 3,853,127 | 12/1974 | Spademan | 128/214.4 |
| 3,994,287 | 11/1976 | Turp et al. | 604/169 |
| 4,000,739 | 1/1977 | Stevens | 128/214.4 |
| 4,177,814 | 12/1979 | Knepshield et al. | 128/348 |
| 4,338,934 | 7/1982 | Spademan | 128/214.4 |
| 4,405,313 | 9/1983 | Sisley et al. | 604/43 |
| 4,424,833 | 1/1984 | Spector et al. | 137/849 |
| 4,430,081 | 2/1984 | Timmermans | 604/256 |
| 4,573,470 | 3/1986 | Samson et al. | 128/344 |
| 4,610,665 | 9/1986 | Matsumoto et al. | 604/167 |
| 4,626,245 | 12/1986 | Weinstein | 604/167 |
| 4,629,450 | 12/1986 | Suzuki et al. | 604/164 |
| 4,634,432 | 1/1987 | Kocak | 604/167 |
| 4,752,287 | 6/1988 | Kurtz et al. | 251/149.1 |
| 4,753,640 | 6/1988 | Nichols et al. | 604/247 |
| 4,842,591 | 6/1989 | Luther | 604/283 |
| 4,895,565 | 1/1990 | Hillstead | 604/167 |
| 4,909,798 | 3/1990 | Fleischhacker et al. | 604/256 |
| 4,917,668 | 4/1990 | Haindl | 604/169 |
| 4,929,235 | 5/1990 | Merry et al. | 604/167 |
| 4,950,257 | 8/1990 | Hibbs et al. | 604/167 |
| 4,960,412 | 10/1990 | Fink | 604/167 |
| 5,000,745 | 3/1991 | Guest et al. | 604/256 |
| 5,053,014 | 10/1991 | Van Heugten | 604/167 |

Primary Examiner—Paul J. Hirsch
Attorney, Agent, or Firm—Sterne, Kessler, Goldstein & Fox

[57] ABSTRACT

An introducer sheath having a hemostatic closure to prevent extracorporeal leakage of blood. In a preferred embodiment, the hemostatic closure includes a support wall which defines an opening having a first region and a second region. The opening is provided with an elastomeric conforming means which conforms to the exterior surface of tubes passed through the hemostatic closure.

19 Claims, 4 Drawing Sheets

INTRODUCER SHEATH HAVING A HEMOSTATIC CLOSURE

FIELD OF THE INVENTION

The present invention relates generally to an introducer sheath for a catheter, and more particularly to an introducer sheath having a hemostatic closure.

BACKGROUND OF THE INVENTION

There are many medical procedures which require the introduction of a cannula or catheter into a major artery or vein for diagnostic purposes. Angioplasty, for example, is a procedure used to treat cardiovascular disease which involves the introduction of a catheter into the common femoral or brachial artery.

Several methods for introducing a catheter into a blood vessel are known in the art. Two such methods include the "cut down" method and the more recent "Seldinger" technique. The cut down method involves surgically opening an artery and introducing a catheter directly into the incision.

The Seldinger technique involves percutaneously inserting a guidewire and a series of cannulas within the lumen of a blood vessel. For angioplasty in particular, a modification of the Seldinger technique, involving the following steps, is employed.

An introducer sheath is introduced into the lumen of the common femoral or brachial artery. A diagnostic catheter with an indwelling guidewire is inserted within the sheath and is advanced through the vessel to the location of the arterial stenosis or occlusion. Once across the stenosis or occlusion, the diagnostic catheter is removed over the guidewire and an angioplasty balloon catheter is placed onto the guidewire and advanced along the length of the wire to the occluded area. The balloon catheter is then inflated with an appropriate medium to recanalize the occluded artery. After a predetermined period of time, the balloon catheter is deflated and removed over the guidewire. The guidewire is usually left within the vessel to reaccess the occluded area if needed. Typically, the angioplasty procedure is evaluated by injecting a radio-opaque fluid into the once-occluded or stenotic artery. This is accomplished by introducing a second catheter and guidewire assembly into the introducer sheath beside the already existing guidewire.

In order to avoid excessive bleeding and air embolisms during the evaluation procedure, the Seldinger technique requires that the Interventional Radiologist block the open end of the introducer sheath. As a result of this reliance upon the radiologist's manual dexterity, the Seldinger technique is often characterized by blood clots, excessive blood loss, venous thrombosis or subcutaneous hematomas.

In an effort to reduce these adverse conditions, several self-sealing introducer sheaths have been developed. For example, U.S. Pat. No. 4,610,665 to Matsumoto et al. discloses a medical instrument having a valve body. The valve body is provided with first and second slits which are openable to receive rod-like members of varying diameters. The valve maintains a liquid-tight state when a rod-like member is inserted through or removed from the main portion of the instrument.

Similarly, U.S. Pat. No. 4,929,235 to Merry et al. discloses an introducer sheath having a sealing mechanism which includes two spaced sealing gaskets adapted to surround a tube. The gaskets are formed from rubber and include a hole or slit.

Still another example of a self-sealing introducer sheath may be found in U.S. Pat. No. 5,000,745 to Guest et al. The Guest et al. patent discloses an introducer sheath having a valve assembly which includes three elastic disc-shaped membranes to sealingly receive a catheter over a guidewire. Each of the three discs is provided with a different type of opening to accommodate passage of a guidewire and catheter therethrough.

Unfortunately, the above-described devices are not well suited for inhibiting blood loss when a catheter is inserted within an introducer sheath beside an existing guidewire (such as when the angioplasty procedure is being evaluated). The valves of each of the above-described devices are incapable of conforming to the outer surfaces of both a guidewire and a catheter placed within an introducer sheath in a side-by-side manner. Thus, there exists a need for a device which prevents blood loss during all stages of the angioplasty procedure.

SUMMARY OF THE INVENTION

In accordance with the purposes of the present invention, as embodied and described herein, the present invention is a hemostatic closure for an introducer sheath including a support means and a conforming means. The support means defines an opening which includes a first region having a first width and a second region having a second width greater than the first width. The conforming means is disposed within the opening, and includes an elastomeric material defining a passage through the conforming means. The elastomeric material conforms to the exterior shape of a tube introduced through the passage defined in the elastomeric material. The opening may be key-hole shaped and the elastomeric material may be rubber. The passage may be in the form of a vertical slit.

In another aspect of the invention, the hemostatic closure includes a conforming means for conforming to the shape of a tube and a support wall disposed about the conforming means. In this embodiment, the conforming means includes a first region having a first width, a second region having a second width greater than the first width, and an elastomeric material which defines a passage through the conforming means. The elastomeric material conforms to the exterior shape of a tube introduced through the passage. The opening may be key-hole shaped and the elastomeric material may be rubber. The passage may be in the form of a vertical slit.

BRIEF DESCRIPTION OF THE DRAWINGS

Various objects, features, and attendant advantages of the present invention will be more fully appreciated as the same becomes better understood from the following detailed description of the present invention when considered in connection with the accompanying drawings, in which.

DETAILED DESCRIPTION OF THE DRAWINGS

Figure 1:
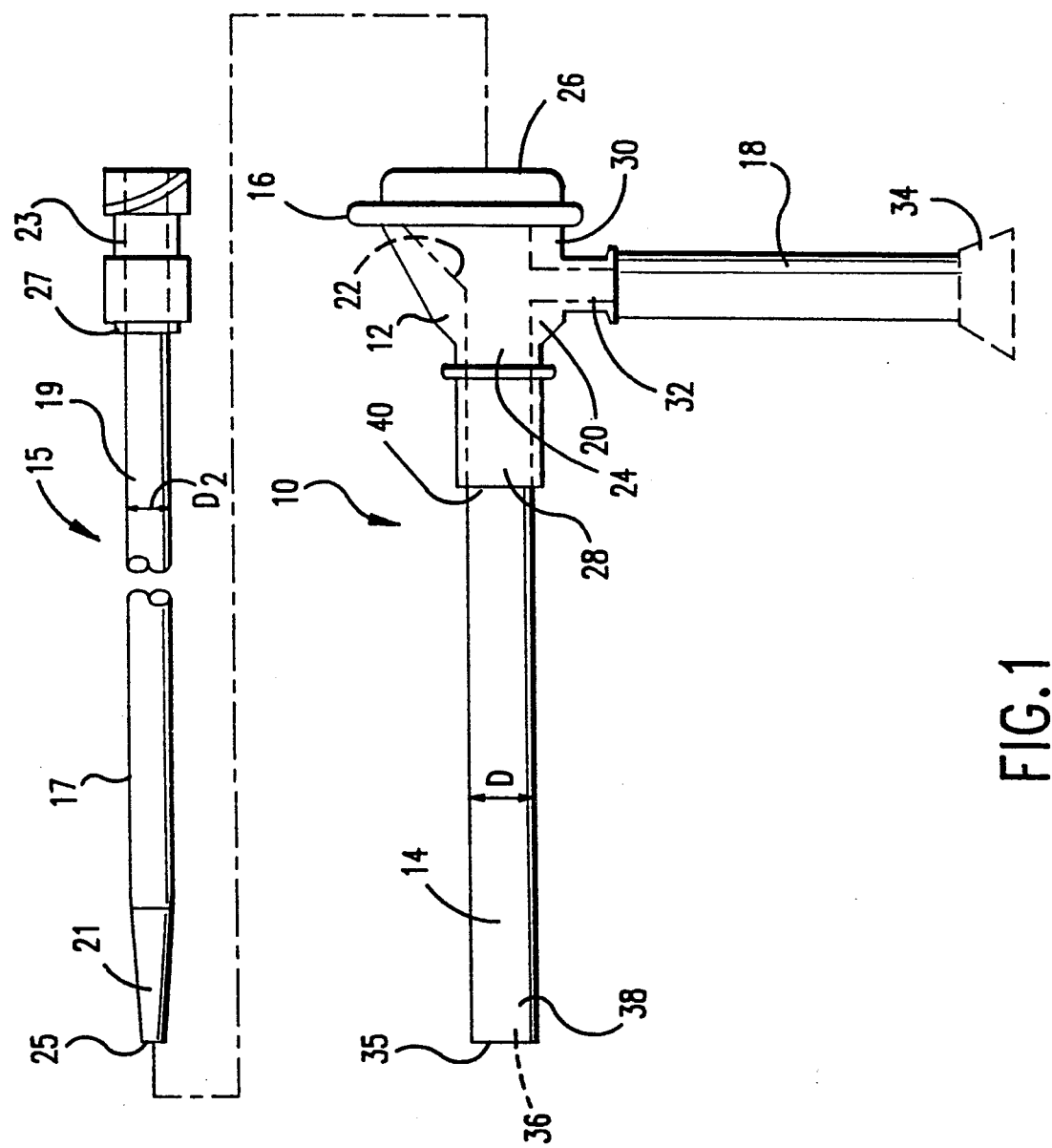
FIG. 1 is a right side elevational view of an introducer sheath including the hemostatic closure of the present invention and a stylet.

With continuing reference to the drawing figures in which similar reference numerals are used throughout the description to describe similar features of the invention, an introducer sheath having a hemostatic closure is shown generally at 10 in FIG. 1. The introducer sheath includes a main body portion 12, a cannula 14, a hemostatic closure 16 and a flexible sidearm tube 18.

In a preferred embodiment, main body portion 12 is substantially frusto-conical in shape and includes an outer surface 20 and an inner surface 22 (shown in phantom). Inner surface 22 defines a central passageway 24 (also shown in phantom) which extends from catheter insertion end 26 of main body portion 12 to cannula engaging end 28. Passageway 24 is structured to accommodate the passage of conventional catheters or other tubular members therethrough. In cross section, passageway 24 is funnel-like in shape. The diameter of passageway 24 is greatest at catheter insertion end 26, approximately 7 mm, and tapers toward cannula engaging end 28 to a diameter of approximately 3 mm. Main body portion 12 may be constructed of any sterilizable, biocompatible material such as stainless steel or plastic, for example.

At its bottom surface 30, main body portion 12 is provided with a fitting 32 which receives a flexible sidearm tube 18. Flexible sidearm tube 18 is in fluid communication with passageway 24 and is provided to introduce heparin or other fluid substances into the blood vessel during the angioplasty procedure. Flexible sidearm tube 18 leads to a stop cock 34 which may be of the type which allows a plurality of fluid flow courses (e.g. a two-way or three-way cock). Flexible sidearm tube 18 may be constructed of any material which is chemically neutral to substances flowing therethrough.

A cannula 14 is provided at cannula engaging end 28 of main body portion 12. Cannula 14 is preferably a flexible tube which includes a wall 35 defining a lumen 36, a blunt distal end 38 and a proximal end 40. Proximal end 40 of cannula 14 is securingly received within main body portion 12 at cannula engaging end 28. Lumen 36 is in communication with and is an extension of passageway 24. In its preferred embodiment, cannula 14 is approximately 8–30 cm in length and has an inner diameter D preferably size 7 French. Cannula 14 may be constructed of any flexible, biocompatible material such as plastic or silicone rubber, for example.

Because distal end 38 of cannula 14 includes a blunt tip, insertion of introducer sheath 10 into the common femoral or brachial artery is assisted by a tapered introducing stylet 15. Stylet 15 includes a wall 17 which defines a central lumen 19, a distal end 21 and a proximal end 23. Outer diameter $D_2$ of stylet 15 is approximately size 7 French. The inner diameter of the stylet is dimensioned to receive a standard 0.038 gauge guidewire which may be introduced into stylet 15 through proximal end 23. The total length of the stylet is preferably 5 cm longer than the total length of cannula 14.

At distal end 21, tip 25 of stylet 15 gradually tapers to a diameter of approximately 1 mm so that stylet 15 may be easily inserted within the artery. At proximal end 23, stylet 15 is provided with a locking mechanism 27 which prevents the stylet from moving within introducer sheath 10 during insertion of the sheath and stylet into the artery.

In use, stylet 15 is inserted within introducer sheath 10 through main body portion 12. The stylet is advanced through passageway 24 and lumen 36 of cannula 14 until locking mechanism 27 engages with a corresponding locking device provided within introducer sheath 10. When the stylet is properly inserted within the introducer sheath, distal end 21 of the stylet extends approximately 5 cm beyond distal end 38 of cannula 14. At this time, the introducer sheath with the indwelling tapered stylet may be easily inserted into the stenotic artery to initiate the angioplasty procedure.

Figure 2:
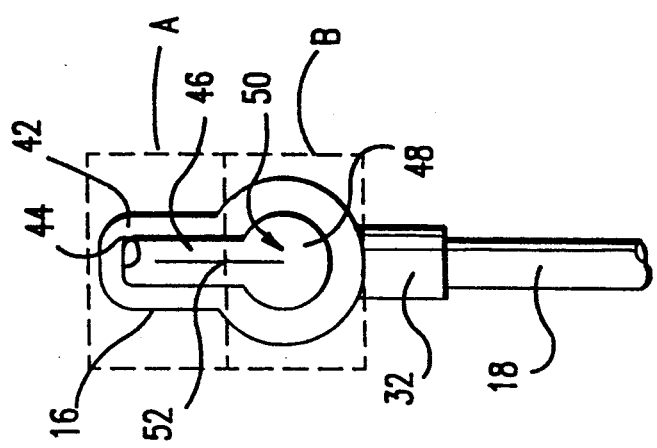
FIG. 2 is a rear elevational view thereof showing the hemostatic closure.

With reference now to FIG. 2, main body portion 12 is fitted with a hemostatic closure 16 at catheter insertion end 26. Hemostatic closure 16 includes a support means 42 which, in its preferred embodiment, defines a key-hole shaped opening 44. The opening 44 has a first region 46 (shown within dashed area A) and a second region 48 (shown within dashed area B). As illustrated in FIG. 2, the width of second region 48 is greater than the width of first region 46. The width of first region 46 is within the range of approximately 1 to 4 mm and is preferably 2 mm wide. The width of second region 48 is within the range of approximately 3 to 5 mm and is preferably 4 mm wide.

A conforming means 50 is provided within opening 44. Conforming means 50 takes the form of a membrane and is constructed of an elastomeric material such as silicone rubber or latex, or any other material capable of conforming to the exterior surface of a tube passed therethrough. The elastomeric material is flexible and is approximately 2 mm thick. Conforming means 50 is provided with a vertical slit or passage 52 which allows the passage of a tube through conforming means 50. Slit 52 extends from first region 46 to second region 48 and is preferably 7 mm in length.

It should be noted that support means 42 may take the form of a wall which surrounds conforming means 50, or inner surface 22 of main body portion 12 may be structured to function as the support means. In any event, the support means is configured such that upon introduction of a tube through slit 52, conforming means 50 exerts a force against the tube. Because of the geometric configuration of opening 44 and support means 42, the force exerted by conforming means 50 is greater in first region 46 due to the greater compression of conforming means 50 in first region 46 of support means 42.

Figure 3:
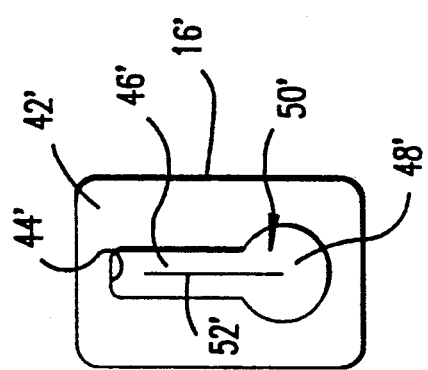
FIG. 3 is an alternate embodiment of the hemostatic closure shown in FIG. 2.

Turning now to FIG. 3, an alternate embodiment of the hemostatic closure illustrated in FIG. 2 is shown. Similar to hemostatic closure 16, hemostatic closure 16' includes a support means 42' which defines an opening 44'. A conforming means 50' is provided within opening 44' and includes a first region 46' and a second region 48'. First and second regions 46' and 48' are dimensioned similar to that of hemostatic closure 16 so that the width of second region 48' is greater than the width of first region 46'.

Conforming means 50' may be constructed from any elastomeric material which is capable of conforming to the outer surface of a tube passed therethrough. Conforming means 50' is provided with a slit 52' which allows a tube to pass through conforming means 50'. Slit 52' extends from first region 46' to second region 48' and is preferably 7 mm in length.

Figure 4:
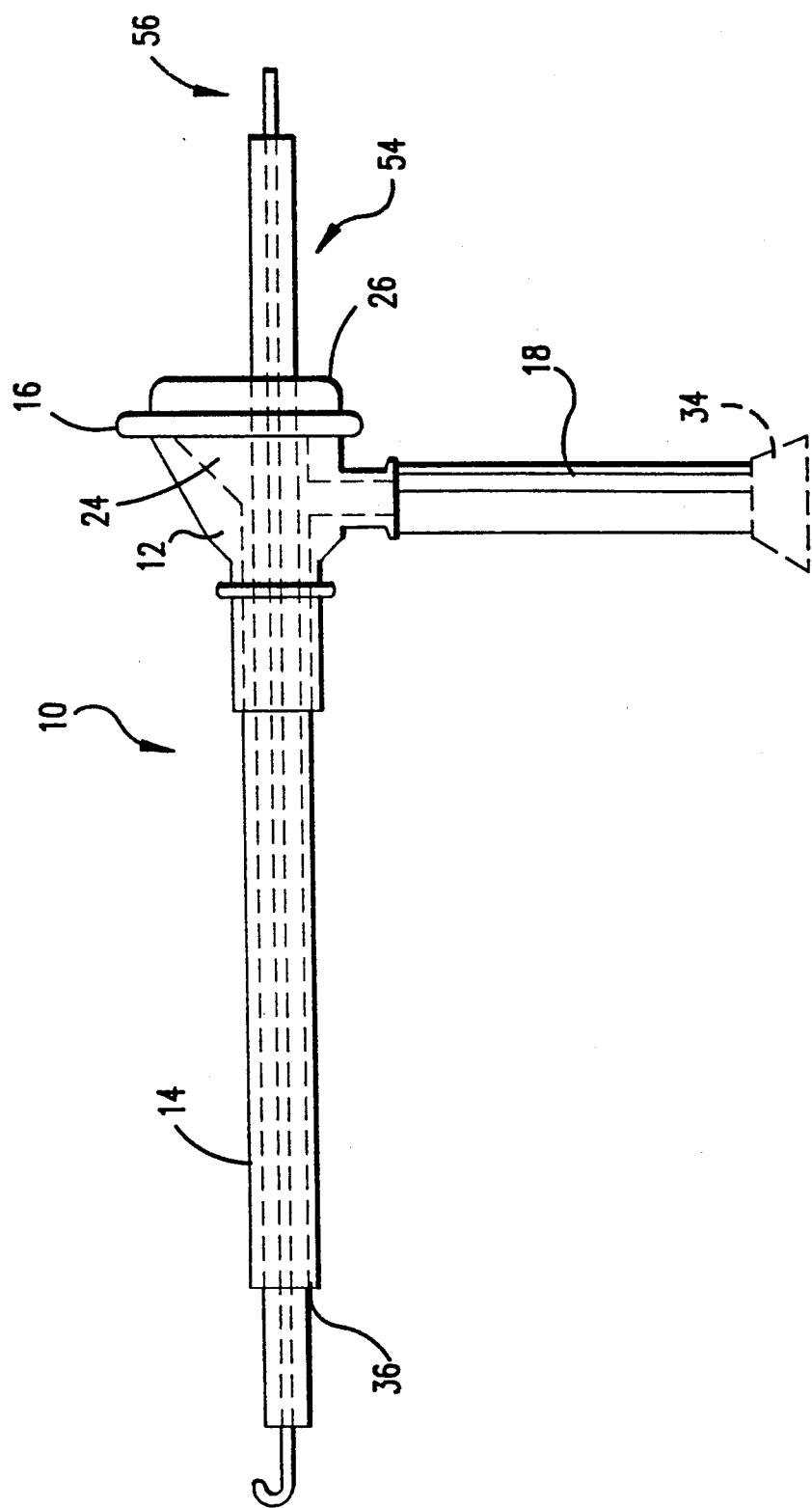
FIG. 4 is a right side elevational view of the introducer sheath shown in FIG. 1 with a first catheter and guidewire inserted therethrough.

With reference now to FIG. 4, introducer sheath 10 including the hemostatic closure of the present invention is shown employed in the following manner. Introducer sheath 10 and stylet 15 (not shown) are introduced into the right or left common femoral artery. Upon entry of introducer sheath 10 into the artery, hemostatic closure 16 is sealed and automatically prevents extracorporeal leakage of blood which has flowed up into cannula 14 and passageway 24. When introducer sheath 10 is properly inserted within the artery, stylet 15 is unlocked from the sheath 10 and removed. As the stylet is removed, hemostatic closure 16 conforms to the stylet's exterior surface to prevent loss of blood. Next, a catheter 54 (shown partially in phantom) with an indwelling guidewire 56 (also shown partially in phantom) is inserted into main body portion 12 of sheath 10 through catheter insertion end 26. Catheter 54 is preferably size 4 or 5 French and is approximately 80 cm in length. Guidewire 56 is preferably formed from 0.035" gauge wire and is approximately 120 to 260 cm in length.

As catheter 54 and guidewire 56 are passed through second region 48 of hemostatic closure 16, the resistance of support means 42 against conforming means 50 assists slit 52 in conforming to the outer surface of catheter 54 to prevent leakage of blood. The catheter and guidewire, now sealingly received within hemostatic closure 16, are advanced through lumen 36 of cannula 14 to the occluded or stenotic area of the artery. Upon reaching the occluded area, catheter 54 is removed over guidewire 56, leaving guidewire 56 in place across the occlusion. As catheter 54 is removed from second region 48, slit 52 of conforming means 50 closes in to seal around the outer surface of guidewire 56, thereby preventing blood loss.

An angioplasty balloon catheter (not shown), preferably size 5 French, is then inserted onto guidewire 56 and is advanced to the site of the stenosis or occlusion. Again, slit 52 of conforming means 50 conforms to the outer surface of the angioplasty catheter as it passes through second region 48 of conforming means 50. The inflatable portion of the balloon catheter is inflated with an appropriate medium, such as air or liquid, to recanalize the occluded artery. After a predetermined period of time, the balloon catheter is deflated and removed over guidewire 56. Guidewire 56 is left across the occlusion to assure reaccess to the area if needed. During this period of time, guidewire 56 is sealingly received within conforming means 50 preventing extracorporeal loss of blood.

Typically, the results of the angioplasty procedure are evaluated by injecting a radio-opaque contrast media into the occluded artery.

Figure 5:
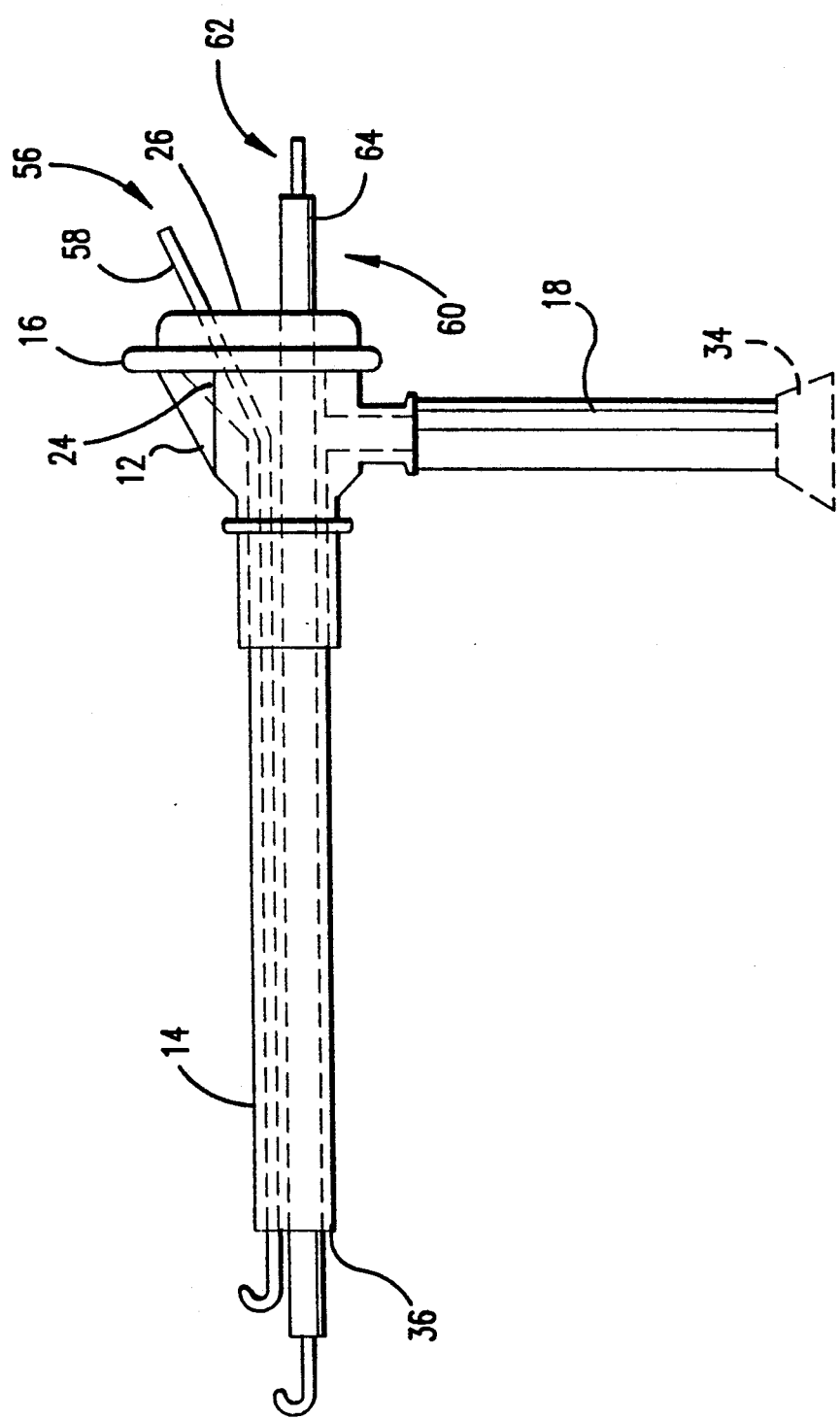
FIG. 5 is a right side elevational view of the introducer sheath shown in FIG. 4 with a second catheter and guidewire inserted beside the original guidewire.

With reference now to FIG. 5, the steps for evaluating the results of the angioplasty procedure will now be described. Guidewire 56 is pulled upward and positioned within first region 46 of conforming means 50. As guidewire 56 is pulled upward, conforming means 50 grips and conforms to exterior surface 58 of guidewire 56 and slit 52 closes as guidewire 56 leaves second region 48.

A second catheter 60 and indwelling guidewire 62 are inserted into main body portion 12 below guidewire 56. Second catheter 60 is preferably size 4 French and is approximately 60 to 80 cm in length. As second catheter 60 and indwelling guidewire 62 pass through second region 48 of hemostatic closure 16, the resistance of support means 42 against conforming means 50 assists slit 52 in conforming to the exterior surface 64 of catheter 60 to prevent leakage of blood.

The catheter and guidewire, now sealingly received within second region 48 of hemostatic closure 16, are passed through lumen 36 to a site adjacent to the once-occluded or stenotic area of the artery. Upon reaching the occluded area, a radio-opaque contrast media is injected into second catheter 60 opacifying the artery at the site of the occlusion. The results of the angioplasty procedure are then evaluated by a radiologic procedure.

Figure 6:
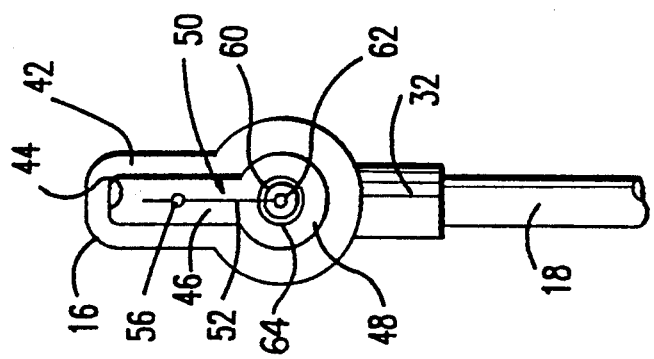
FIG. 6 is a rear view elevational thereof showing the second catheter and guidewire and the original guidewire within the hemostatic closure.

As can be seen in FIG. 6, original guidewire 56 and second catheter 60 are both sealingly received within hemostatic closure 16. Unlike other devices, the hemostatic closure of the present invention is capable of sealingly receiving a catheter and guidewire inserted through the slit in a side-by-side manner. This is accomplished in part because of the specific configuration of support means 42 (or with regard to the embodiment shown in FIG. 3, because of the dimensions of first and second regions 46' and 48' respectively). In first region 46, support wall 42 resists against conforming means 50 to allow slit 52 to sealingly conform about the outer surface of a guidewire or other small tubular member. In second region 48, support wall 42 provides enough resistance against conforming means 50 to allow slit 52 to sealingly conform about the outer surface of a catheter or other similarly-sized tube. Where there is no tube passing through conforming means 50, support wall 42 provides a sufficient amount of resistance against conforming means 50 to completely seal or close slit 52. Thus, the hemostatic closure of the present invention allows a catheter and guidewire to be inserted within an introducer sheath in a side by side manner while still effectively preventing significant extracorporeal loss of blood.

Although not specifically discussed, it should be realized that hemostatic closure 16' (shown in FIG. 3) is utilized within an introducer sheath in substantially the same manner to prevent blood loss during the angioplasty procedure.

Furthermore, while the present invention has been disclosed in connection with the preferred embodiment thereof, it should be understood that there are other embodiments which fall within the spirit and scope of the invention as defined by the following claims. For example, the objective of the present invention may also be carried out by forming the first and second region of the closure from elastomeric materials of varying durometers to conform to the outer surface of tubes passed therethrough. In this embodiment in particular, the closure could be formed without a distinct opening and need not be substantially keyhole shaped.

I claim:

1. A hemostatic closure for an introducer sheath, comprising:
    (a) a support means, said support means defining an opening, wherein said opening includes a first region having a first width and a second region having a second width greater than said first width; and
    (b) conforming means disposed within said opening, said conforming means comprising an elastomeric material defining a passage through said elastomeric material, wherein said elastomeric material is capable of conforming to the exterior shape of adjacent tubular members passed through said passage.

2. The hemostatic closure of claim 1, wherein said elastomeric material is rubber.

3. The hemostatic closure of claim 1, wherein said opening is key-hole shaped.

4. The hemostatic closure of claim 1, wherein said passage is a slit.

5. The hemostatic closure of claim 1, wherein said tubular members are catheters, cannulas or guidewire.

6. The hemostatic closure of claim 1, wherein said width of said first region is within the range of approximately 1 mm to 4 mm.

7. The hemostatic closure of claim 6, wherein said width of said first region is approximately 2 mm.

8. The hemostatic closure of claim 1, wherein said width of said second region is within the range of approximately 3 mm to 5 mm.

9. The hemostatic closure of claim 8, wherein said width of said second region is approximately 4 mm.

10. A hemostatic closure for an introducer sheath, comprising:
    (a) a conforming means, said conforming means including
        (1) a first region having a first width;
        (2) a second region having a second width greater than said first width; and
        (3) an elastomeric material defining a passage through said elastomeric material, wherein said elastomeric material is capable of conforming to the exterior shape of adjacent tubular members passed through said passage; and
    (b) a support wall disposed about said conforming means for providing support to said conforming means.

11. The hemostatic closure of claim 10, wherein said elastomeric material is rubber.

12. The hemostatic closure of claim 10, wherein said opening is key-hole shaped.

13. The hemostatic closure of claim 10, wherein said passage is a slit.

14. The hemostatic closure of claim 10, wherein said tubular members are catheters, cannulas or guidewire.

15. The hemostatic closure of claim 10, wherein said width of said first region is within the range of approximately 1 mm to 4 mm.

16. The hemostatic closure of claim 15, wherein said width of said first region is approximately 2 mm.

17. The hemostatic closure of claim 10, wherein said width of said second region is within the range of approximately 3 mm to 5 mm.

18. The hemostatic closure of claim 17, wherein said width of said second region is approximately 4 mm.

19. A hemostatic closure for an introducer sheath, comprising:
    (a) a support means, said support means including a first region having a first width and a second region having a second width greater than said first width, said first region and said second region being vertically aligned;
    (b) means for conforming to the shape of a tube disposed within and completely filling said first and second regions, said conforming means comprising an elastomeric material defining a passage therethrough, wherein said elastomeric material conforms to the exterior shape of a tube upon introduction of said tube through said passage.

* * * * *